(12) United States Patent
Olmo et al.

(10) Patent No.: US 9,339,350 B2
(45) Date of Patent: May 17, 2016

(54) MIXING DEVICE FOR A DENTAL POWDER JET APPARATUS, AND DENTAL HAND-HELD INSTRUMENT FOR A POWDER JET APPARATUS INCLUDING A RESPECTIVE MIXING DEVICE

(75) Inventors: Olivier Olmo, Morges (CH); Marcel Donnet, Saint Jean de Gonville (FR)

(73) Assignee: FERTON HOLDING S.A. (CH)

( * ) Notice: Subject to any disclaimer, the term of this patent is extended or adjusted under 35 U.S.C. 154(b) by 241 days.

(21) Appl. No.: 13/527,178

(22) Filed: Jun. 19, 2012

(65) Prior Publication Data

US 2012/0329005 A1 Dec. 27, 2012

(30) Foreign Application Priority Data

Jun. 22, 2011 (DE) .......................... 10 2011 077 995

(51) Int. Cl.
*A61C 3/025* (2006.01)

(52) U.S. Cl.
CPC ...................... *A61C 3/025* (2013.01)

(58) Field of Classification Search
CPC ........................................................ A61C 3/025
USPC ..................................................... 433/80–88
See application file for complete search history.

(56) References Cited

U.S. PATENT DOCUMENTS

| | | | | |
|---|---|---|---|---|
| 2,759,266 A | * | 8/1956 | Cassani | ........................... 433/88 |
| 4,696,645 A | * | 9/1987 | Saupe | .................... A61C 3/025 433/125 |
| 5,718,581 A | * | 2/1998 | Fernwood | .............. A61C 3/025 222/196 |
| 5,857,851 A | | 1/1999 | Chavanne | |
| 6,139,320 A | * | 10/2000 | Hahn | ............. A61B 17/320068 433/119 |
| 2001/0031441 A1 | * | 10/2001 | Ito | ........................... A61C 3/025 433/88 |
| 2002/0077041 A1 | * | 6/2002 | Groman | ................ B24C 7/0046 451/75 |
| 2003/0003849 A1 | * | 1/2003 | Groman | ................ A61C 3/025 451/36 |
| 2003/0219695 A1 | * | 11/2003 | Rasmussen | ............ A61C 3/025 433/88 |
| 2005/0202364 A1 | * | 9/2005 | Fornasari | ............... A61C 3/025 433/88 |
| 2006/0205330 A1 | * | 9/2006 | Groman | .................... B24C 5/02 451/90 |
| 2009/0246730 A1 | | 10/2009 | Takamori et al. | |
| 2012/0171636 A1 | * | 7/2012 | Groman | ................ A61C 3/025 433/83 |

FOREIGN PATENT DOCUMENTS

| | | |
|---|---|---|
| DE | 197 42 701 | 4/1998 |
| DE | 197 14 276 | 10/1998 |
| EP | 0 119 735 | 9/1984 |
| EP | 0 834 291 | 4/1988 |
| EP | 2 036 513 | 3/2009 |
| FR | 2 588 182 | 4/1987 |
| GB | 1 420 386 | 1/1976 |

OTHER PUBLICATIONS

European Search Report dated Sep. 18, 2012 of European Patent Application 12 170 940.6.

* cited by examiner

*Primary Examiner* — Cris L Rodriguez
*Assistant Examiner* — Hao D Mai
(74) *Attorney, Agent, or Firm* — Ostrolenk Faber LLP

(57) ABSTRACT

A mixing device for a dental powder jet device, comprising a receptacle for receiving a powder, an inlet for a transport fluid, and an outlet for a powder/transport fluid mixture, the outlet comprising at least one outlet nozzle, the inlet comprising at least one first and at least one second inlet nozzles wherein the outflow direction of the first inlet nozzle intersects the inflow direction of the outlet nozzle, and wherein the outflow direction of the second inlet nozzle is arranged in an offset manner with respect to the outflow direction of the first inlet nozzle.

17 Claims, 5 Drawing Sheets

MIXING DEVICE FOR A DENTAL POWDER JET APPARATUS, AND DENTAL HAND-HELD INSTRUMENT FOR A POWDER JET APPARATUS INCLUDING A RESPECTIVE MIXING DEVICE

BACKGROUND

The present invention relates to a mixing device for a dental powder jet apparatus and a dental hand-held instrument for a powder jet apparatus including a respective mixing device.

RELATED ART

Mixing devices of the related type are well known in the art. Accordingly, as shown in FIGS. 6-8, U.S. Pat. No. 5,857, 851 (DE197 14 276 A1), incorporated by reference, discloses for example a handpiece (1) with a mixing device (powder container 2) consisting of a mixing chamber (hemispheres 3, 4) formed as a rotational hollow body, the end of a feed line for compressed air and water (coupling 12; col. 3, lines 41-46) and a transfer line (15) coupled to a multiple nozzle arrangement (11) on a spraying head (10) of a gripping sleeve (5), for spraying the powder/air mixture which is formed in the interior of the rotational hollow body entering the internal space thereof. However a problem arises with such arrangements in that during operation of the mixing device homogenous generation of the powder/air mixture cannot be assured nor may a consistent mixing ratio over time during operation independently of the powder filling level be guaranteed.

SUMMARY

It is thus an object of the present invention to provide a mixing device for a dental powder jet device as well as a dental hand-held instrument for a powder jet device which, independently of the powder filling level, will provide a powder/fluid mixture which is as homogenous as possible, not varying qualitatively and quantitatively.

This object will be solved by a mixing device for a dental powder jet device as well as a dental hand-held instrument for a powder jet device as disclosed herein. Preferred embodiments are also disclosed.

According to the invention a mixing device for a dental powder jet device is provided comprising a receptacle for receiving a powder, an inlet for a transport fluid, and an outlet for a powder/transport fluid mixture, the outlet having at least one outlet nozzle, the inlet having at least a first and a second inlet nozzle, wherein the outflow direction or jet-ejection direction, respectively, from the first inlet nozzle intersects the inflow direction or jet-injection direction, respectively, into the outlet nozzle; and the outflow direction or jet-ejection direction, respectively, from the second inlet nozzle is aligned in an offset manner with respect to the outflow direction or jet-ejection direction, respectively, from the first inlet nozzle. The mixing device especially serves as a mixing and/or turbulence chamber in order to allow mixing or turbulence, respectively, of the powder into the transport fluid to take place. The transport fluid may be a gas, for example air, or a fluid, for example water, or a combination of the same. The inlet serves for feeding the transport fluid into the receptacle. The outlet serves for discharging the mixture of powder and transport fluid from the receptacle into a hand piece of a dental powder jet device. For this the outlet has at least one outlet nozzle which is located in the internal space of the receptacle. It is understood that a variety of outlet nozzles may also be provided. The outlet nozzle may be formed as a hole or rupture in an outlet part provided in the receptacle. Similarly the inlet has at least a first and a second inlet nozzle. The latter are also located in the internal space of the receptacle. As to their cross section the first and second inlet nozzle may also be formed as a hole, rupture, or slot. It is understood that the form and size of the cross section of the first and second inlet nozzle as well as the outlet nozzle may be formed equally or differently. According to the invention the outflow direction or jet-ejection direction, respectively, of the first inlet nozzle intersects and/or crosses and/or traverses the inflow direction or jet-injection direction, respectively, into the outlet nozzle. In other words the flow directions of the transport fluid exiting the first inlet nozzle and the powder/transport fluid mixture flowing into the outlet nozzle intersect each other. The respective inflow and outflow directions, respectively, may be a notional straight line of the current and/or flow directions prevailing in the region of the entry and/or the exit of the respective nozzle. Advantageously, in a preferred embodiment, the respective nozzles do not have to be adjacent to each other, i.e. for example they do not have to level with the receptacle. Suitably the transport fluid does not exit the inlet nozzles in a linear way nor does the powder/transport fluid mixture enter into the outlet nozzle in a linear way but in a way which follows the flow cover. For this, the lines of symmetry (i.e. rotational symmetry lines of the flow covers) of the outflow direction of the first inlet nozzle and the inflow direction of the outlet nozzle do not have to intersect each other but may be offset to each other by an angular dimension of up to 15°, preferably up to 10° and most preferably about 5°-7°. In other words, the inlet—starting from a position wherein the lines of symmetry of the outflow direction of the first inlet nozzle and the inflow direction of the outlet nozzle intersect each other—may be rotated by the aforementioned angular dimension. It will be especially preferred if the flow cover especially of the outflow direction or jet-ejection direction, respectively, of the transport fluid will be formed in a range of up to about 25°, preferably up to 20° and most preferably up to about 15°. Suitably the flow cover extends—starting from the respective nozzle—into the receptacle at least 20 times, preferably at least 50 times and especially preferred at least 100 times the length of the respective nozzle diameter. The extension of the flow cover may also be referred to as an open jet. The diameter of the outlet nozzle will suitably be in the range of 0.35 to 0.75 mm, preferably 0.4 to 0.6 mm. The diameter of the inlet nozzles will suitably be in the range of 0.4 to 0.8 mm, preferably 0.6 to 0.7 mm. In a preferred embodiment the outflow direction or jet-ejection direction, respectively, of the first inlet nozzle is directed toward the outlet nozzle. In other words the outflow direction or jet-ejection direction, respectively, of the first inlet nozzle may intersect the port of the outlet nozzle. Furthermore the outflow direction or jet-ejection direction, respectively, of the second inlet nozzle is aligned in an offset manner with respect to the outflow direction or jet-ejection direction, respectively, of the first inlet nozzle. The outflow direction of the first inlet nozzle and the outflow direction of the second inlet nozzle may thereby be located in the same plane, both outflow directions being suitably arranged in an angular position to each other. Advantageously the angle will not be 0° or 180°, in other words, the outflow directions will preferably be non-parallel if they are located in one plane. Especially preferred the outflow directions of both the first and second inlet nozzle will not only be arranged in an angular position to each other but will additionally be located in different planes. By way of this arrangement it is assured that the powder/transport fluid mixture will be homogenous, not being affected by the powder filling level in the receptacle. This will especially be accomplished by forming the first inlet nozzle such that the outlet nozzle will be kept free of powder, by way of blowing part of the transport fluid past the outlet nozzle by the first inlet nozzle thus avoiding accumulation of powder at or directly in front of the outlet nozzle. In order to assure the required supply of powder to the outlet nozzle the second inlet nozzle is provided. The latter serves as a so called turbulence nozzle conferring turbulence to the powder in the receptacle. It will thereby be of advantage that in a preferred embodiment no particular position of the second inlet nozzle will be required with respect to the receptacle and/or powder located in the receptacle. In other words the second inlet nozzle does not have to be directed towards or at least does not have to be directly directed towards the powder. Consequently, it does for example not have to be directed downwardly.

Suitably the first inlet nozzle is arranged in closer neighborhood to the outlet nozzle than the second inlet nozzle. In other words the distance the transport fluid has to travel to the outlet nozzle is shorter starting from the first inlet nozzle than from the second inlet nozzle.

Advantageously the mixing device is formed such that the outflow direction of the second inlet nozzle will not intersect the inflow direction of the outlet nozzle and will not be axially aligned with it. It may thus be provided that the flow directions of the second inlet nozzle and the outlet nozzle are in fact arranged in parallel but offset to each other such that they will not be axially aligned to each other. However it is of particular advantage if they are not arranged in parallel but in an angle to each other not equaling 0° or 180°, with no intersection of the outflow directions of the second inlet nozzle and the outlet nozzle being present.

Advantageously the outflow direction of the second inlet nozzle will not intersect the outflow direction of the first inlet nozzle. The first and second inlet nozzles may especially be arranged for this, such that they won't be arranged in a common plane. Additionally or alternatively they also may be offset to each other such that they (considering parallel flow direction) will be located in the same plane with the flow directions not intersecting themselves.

In another preferred embodiment the outflow directions of the first and second inlet nozzle are arranged in an angle of about 60°-120°, preferably about 80°-100° and most preferred about 90° to each other. By arranging the flow directions in an angle of about 90° an especially advantageous homogenous mixing ratio of transport fluid and powder will be assured.

Moreover, the inlet is preferably formed as a tubular body onto which the first and second inlet nozzles are arranged in the flow direction of the transport fluid in an offset manner. The tubular body may therefore be frontally closed, so that the inlet nozzles will be provided on the lateral surface thereof. It is understood that one of those inlet nozzles may also be provided on the frontal side of the tubular body whereas the remaining inlet nozzle is formed on the lateral surface thereof. The flow direction of the transport fluid essentially corresponds to the longitudinal extension of the tubular body. Most advantageously the second inlet nozzle—as seen in the flow direction of the transport fluid—is more distant from the outlet nozzle than the first inlet nozzle. In other words the first inlet nozzle is suitably arranged downstream of the second inlet nozzle.

In an alternative embodiment the inlet is formed of a first tubular body which comprises the first inlet nozzle, a second tubular body which comprises the second inlet nozzle. The inlet nozzles may be formed on the front side of the respective first and/or second tubular body. Additionally or alternatively the inlet nozzles may also be formed on the respective lateral surface of the first and/or second tubular body. It is understood that the first tubular body and the second tubular body may enter into a common lead in the interior or exterior of the receptacle for supplying the transport fluid.

Suitably the inlet advantageously has an even multitude, preferably two, first and/or second inlet nozzles which each are oppositely arranged. In other words, advantageously one or more pairs of first inlet nozzles or one or more pairs of second inlet nozzles, respectively, each are provided, wherein the inlet nozzles of one pair may suitably be oppositely arranged to each other.

Preferably the outlet has a multitude, preferably two to ten, more preferably three to six and most preferably four outlet nozzles which suitably are arranged linearly to each other. The outlet nozzles are preferably arranged such that said outlet nozzles are located on a straight line. Most suitably the outlet nozzles are configured such that the outflow directions thereof will be arranged in parallel to each other.

Preferably the outlet is formed as a tubular body on the lateral surface of which the at least one outlet nozzle is provided in the form of a bore and the frontal side of which is preferably closed. Thereby a mixing device will be enabled which is extremely easy to manufacture.

Advantageously the total surface area of the openings of the first and second inlet nozzles exceeds the total surface area of the openings of the at least one outlet nozzle. It will thereby be assured that the parameter of mixing of the powder/transport fluid mixture as well as of the amount of the powder/transport fluid mixture to be supplied to the outlet will be defined and controlled both by the surface area and configuration of the openings of the outlet nozzle.

Moreover the total surface area of the openings of the at least one first inlet nozzle advantageously exceeds the total surface area of the openings of the at least one second inlet nozzle. It thereby will be assured that the outlet nozzle will reliably be kept free of accumulations of powder.

Furthermore, according to the invention, a dental handheld instrument for a powder jet device is provided, comprising a hand-held part including a hand piece having a gripping part on the front side of which an outlet opening for a powder/transport fluid mixture is provided, and a coupling connection for connecting a mixing device, the mixing device having a receptacle for receiving a powder, an inlet for a transport fluid, and an outlet for a powder/transport fluid mixture, the outlet having at least one outlet nozzle, the inlet having at least a first and a second inlet nozzle, wherein the outflow direction of the first inlet nozzle intersects the inflow direction of the outlet nozzle and the outflow direction from the second inlet nozzle is aligned in an offset manner with respect to the outflow direction of the first inlet nozzle. The dental handheld instrument thus has a hand piece on which a gripping part is arranged, wherein with respect to the gripping part an outlet opening is frontally provided wherefrom the powder, which suitably is formed as an abrasive treatment agent, and the transport fluid may be released.

It is understood that further advantages and features of the mixing device according to the invention as well as preferred embodiments thereof may be an object of the dental handheld instrument according to the invention.

BRIEF DESCRIPTION OF THE DRAWINGS

Further advantages and characteristics will arise from the specification below of preferred embodiments of the invention while reference will be made to the accompanying figures wherein individual characteristics of individual embodiments may be combined into new embodiments, wherein.

DETAILED DESCRIPTION

Figure 1:
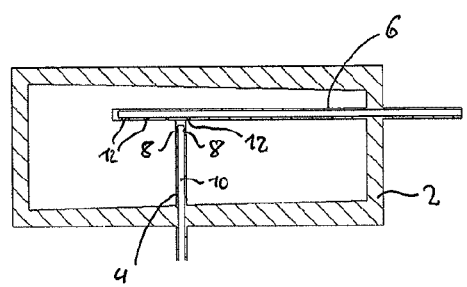
FIG. 1 shows a cross section of a first illustrative embodiment of the mixing device according to the invention.

In FIG. 1 a first illustrative embodiment of a mixing device according to the invention including a receptacle 2, an inlet 4 as well as an outlet 6 is shown.

The receptacle 2 is formed as a turbulence chamber and serves for the turbulence of and/or mixing a powder (not shown) provided in the receptacle 2. An inlet 4 for a transport fluid, for example air, water or a mixture thereof protrudes into the receptacle 2. The inlet is formed as a tubular body including a pair of each of first inlet nozzles 8 and second inlet nozzles 10 which are located opposite to each other. The outlet 6 is similarly formed as a tubular body protruding into the receptacle 2. Both inlet 4 and outlet 6 are frontally closed. Four outlet nozzles 12 are connected to the lateral surface. On the lateral surface of the outlet 6 four outlet nozzles 12 are formed. The latter are formed in the direction of and/or in parallel to inlet 4 which is formed as a tubular body.

Figure 2:
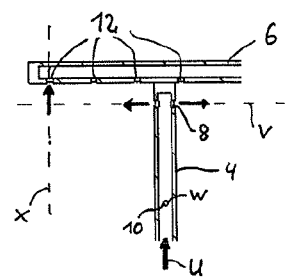
FIG. 2 shows an enlarged partial view of FIG. 1.

As it becomes obvious from FIG. 2 the first inlet nozzle 8 is offset with respect to the second inlet nozzle 10 in the flow direction U of the transport fluid such that the second inlet nozzle 10 is arranged in front of the first inlet nozzle 8 as viewed in the flow direction U. The first inlet nozzle 8 comprises an outflow direction V and the second inlet nozzle 10 comprises an outflow direction W. The outflow directions V, W are aligned in an offset manner with respect to each other such that they will not intersect each other. In the embodiment as set forth the outlet nozzles 12 are arranged along a straight line such that the inflow directions X thereof are arranged in parallel to each other. In order to assure the outlet nozzles 12 to be free of powder the outflow direction V of the first inlet nozzle 8 intersects the inflow directions X of the outlet nozzles 12.

Figure 3:
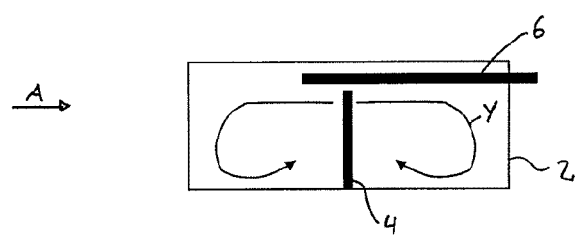
FIG. 3 shows a schematic view according to FIG. 1.
Figure 4:
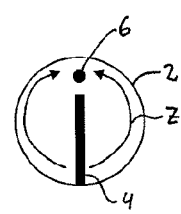
FIG. 4 shows a schematic view in the arrow direction A from FIG. 3.

This causes turbulence of the powder in the receptacle 2 as it is shown in FIGS. 3 and 4. The first inlet nozzles 8 cause turbulence of the powder, the turbulence being parallel with respect to the orientation of the outlet 6 and away from it, as it is represented by the arrows Y. In order to supply a predetermined amount of powder to the outlet nozzle 12 the second inlet nozzles 10 cause turbulence, as it is shown by the arrow Z. The turbulence Z is perpendicular to the turbulence represented by the arrow Y and in the bottom-up direction with respect to the outlet nozzle 12 and outlet 6, respectively.

Figure 5:
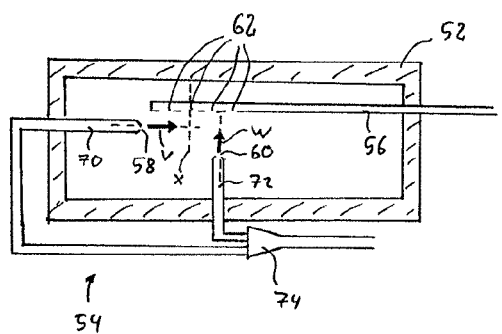
FIG. 5 shows a cross sectional view of another preferred embodiment of the mixing device according to the invention.
Figure 6:
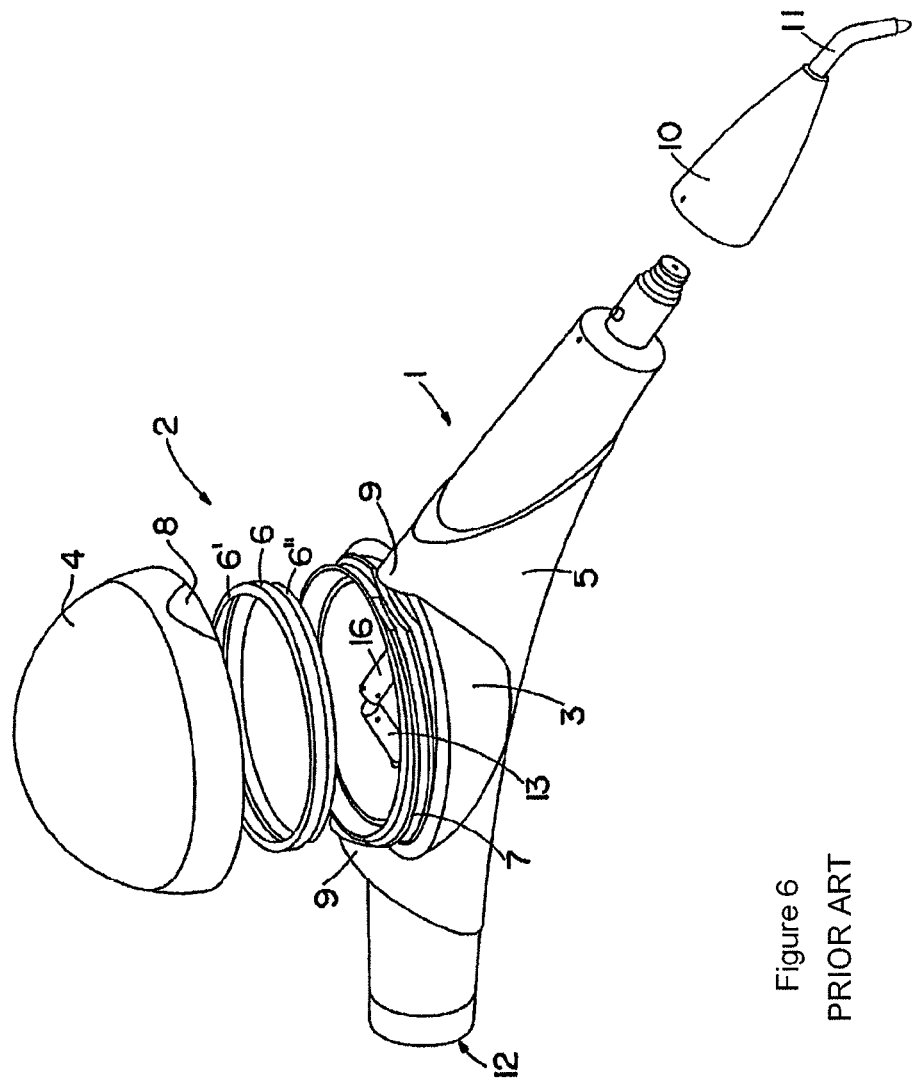
FIG. 6 shows a perspective view with a partwise exploded illustration of a prior art handpiece having an integrated powder container in the form of a hollow sphere.
Figures 7, 8:
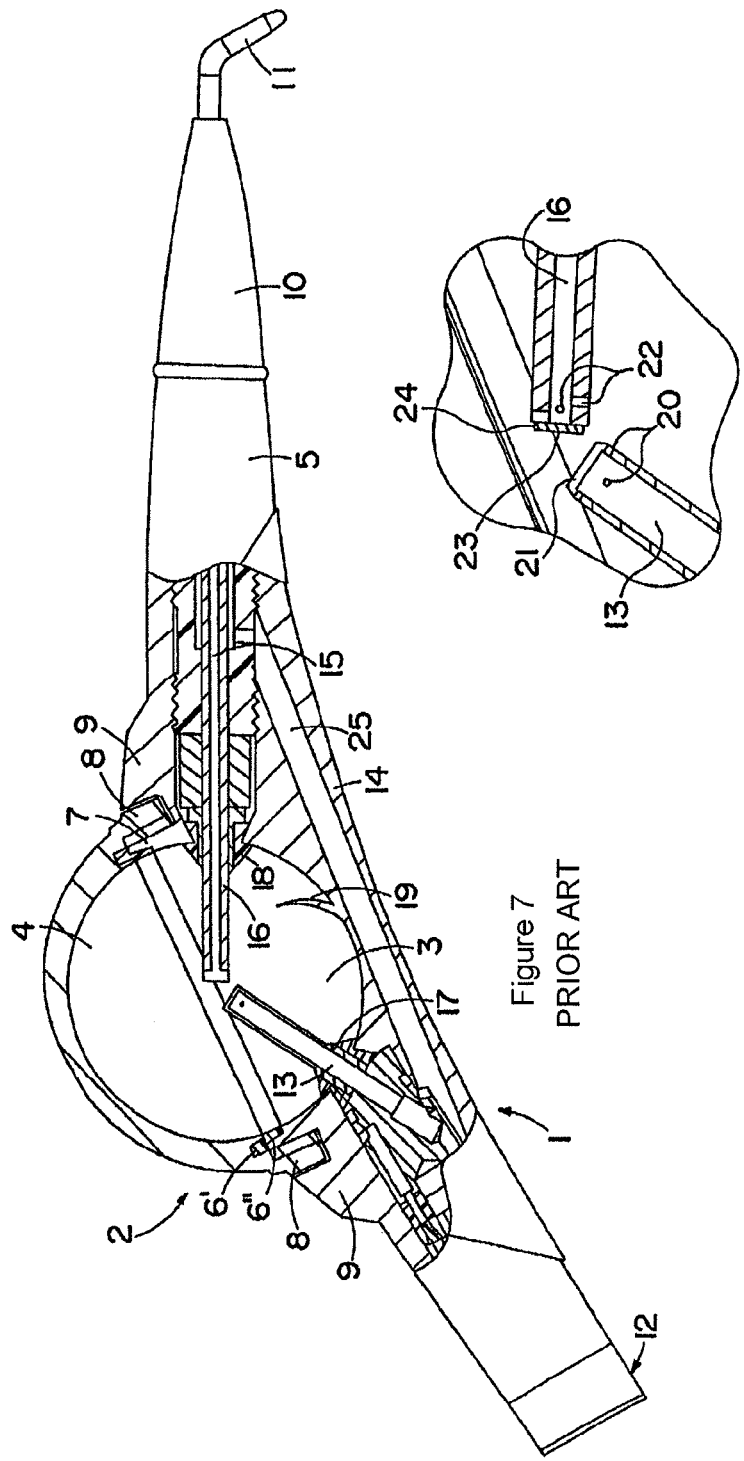
FIG. 7 shows a partwise sectioned general view of the prior art hand-piece.
FIG. 8 shows a sectional view of the outlet and the inlet ends as formed by tubular pieces of the supply line for pressurized air and of the transfer line for the powder and air mixture respectively of the handpiece of FIGS. 6 and 7.

In FIG. 5 another illustrative embodiment of the mixing device according to the invention is shown. Similar to the embodiment represented in FIG. 1a receptacle 52 formed as a turbulence chamber is provided, in which an outlet 56 having appropriately arranged outlet nozzles 62 is communicatingly provided. The inlet 54, however, is formed of a first tubular body 70 and a second tubular body 72 which are in a shared manifold 74 at the outer side of the receptacle 52. The first tubular body 70 protrudes into the receptacle 52 in an essentially parallel arrangement with respect to the outlet 56 and is provided with the first inlet nozzle 58 at its front side. The second tubular body essentially protrudes into the receptacle 52 perpendicular to the extension of outlet 56 and is provided with the second inlet nozzle 60 at its front side.

As it can be seen the outflow direction V of the first inlet nozzle 58 intersects the inflow direction X of the outlet nozzle 62. It hereby will be assured that the outlet nozzle 62 will be kept free from undesired accumulation of powder. In order to supply the predetermined amount of powder to the outlet nozzle 62 the outflow direction W of the second inlet nozzle 60 is arranged such that the former, i.e. the outflow direction W and the inflow direction X are in fact arranged in parallel to each other but do not intersect each other nor are they axially aligned to each other.

Although the present invention has been described in relation to particular embodiments thereof, many other variations and modifications and other uses will become apparent to those skilled in the art. Therefore, the present invention is not limited by the specific disclosure herein.

LIST OF REFERENCE NUMBERS 2 receptacle
4 inlet
6 outlet
8 first inlet nozzle
10 second inlet nozzle
12 outlet nozzle
52 receptacle
54 inlet
56 outlet
58 first inlet nozzle
60 second inlet nozzle
62 outlet nozzle
70 first tubular body
72 second tubular body
74 manifold
U flow direction
V outflow direction
W outflow direction
X inflow direction
Y, Z turbulence directions

The invention claimed is:

1. A mixing device for a dental powder jet device, comprising:
    a receptacle for receiving a powder,
    an inlet for a transport fluid, and
    an outlet for a powder/transport fluid mixture,
    the outlet having at least one outlet nozzle,
    the inlet having at least one first inlet nozzle and at least one second inlet nozzle,
    wherein an outflow direction (v) of the at least one first inlet nozzle is directed toward the at least one outlet nozzle,
    wherein an outflow direction (v) of the at least one first inlet nozzle intersects an inflow direction (x) of the at least one outlet nozzle, and
    wherein an outflow direction (w) of the at least one second inlet nozzle and the outflow direction (v) of the at least one first inlet nozzle are directed in an angular relation to each other and/or in different planes.

2. The mixing device according to claim 1, wherein the at least one first inlet nozzle is arranged closer to the at least one outlet nozzle than the at least one second inlet nozzle.

3. The mixing device according to claim 1, wherein the outflow direction (w) of the at least one second inlet nozzle does not intersect and is not axially aligned to the inflow direction (x) of the at least one outlet nozzle.

4. The mixing device according to claim 1, wherein the outflow direction (w) of the at least one second inlet nozzle does not intersect the outflow direction (v) of the at least one first inlet nozzle.

5. The mixing device according to claim 1, wherein the outflow directions (v, w) of the at least one first inlet nozzle and the at least one second inlet nozzle are arranged at an angle of about 60° to 120° to each other.

6. The mixing device according to claim 5, wherein the outflow directions (v,w) of the at least one first inlet nozzle and the at least one second inlet nozzle are arranged at an angle of about 80° to 100° to each other.

7. The mixing device according to claim 6, wherein the outflow directions (v,w) of the at least one first inlet nozzle and the at least one second inlet nozzle are arranged at an angle of about 90° to each other.

8. The mixing device according to claim 1, wherein the inlet is formed as a tubular body on which the at least one first inlet nozzle and the at least one second inlet nozzle are arranged offset in a flow direction (u) of the transport fluid.

9. The mixing device according to claim 1, wherein the inlet is formed of a first tubular body comprising the at least one first inlet nozzle and a second tubular body comprising the at least one second inlet nozzle.

10. The mixing device according to claim 1, wherein said at least one first inlet nozzle comprises two first inlet nozzles and/or said at least one second inlet nozzle comprises two second inlet nozzles.

11. The mixing device according to claim 10, wherein the two first inlet nozzles are arranged oppositely to each other and the two second inlet nozzles are arranged oppositely to each other.

12. The mixing device according to claim 1, wherein the outlet is formed as a tubular body having lateral surfaces on which the at least one outlet nozzle is provided in the form of respective bores.

13. The mixing device according to claim 12, wherein a front side of said tubular body is closed.

14. The mixing device according to claim 1, wherein a total surface area of openings of the at least one first inlet nozzle and the at least one second inlet nozzle exceeds a total surface area of an opening of the at least one outlet nozzle.

15. The mixing device according to claim 1, wherein a total surface area of an opening of the at least one first inlet nozzle exceeds a total surface area of an opening of the at least one second inlet nozzle.

16. The mixing device according to claim 1, wherein said at least one outlet nozzle comprises two or ten outlet nozzles which are arranged aligned with each other along a length of said outlet.

17. A dental hand-held instrument for a powder jet device, comprising:
a hand piece having a gripping part on the front side of which an outlet opening for a powder/transport fluid mixture is provided,
a mixing device, and
a coupling connection configured for connecting the hand piece to the mixing device,
the mixing device comprising a receptacle for receiving a powder, an inlet for a transport fluid, and an outlet for a powder/transport fluid mixture,
the outlet comprising at least one outlet nozzle,
the inlet comprising at least one first inlet nozzle and at least one second inlet nozzle,
wherein an outflow direction (v) of the at least one first inlet nozzle intersects an inflow direction (x) of the at least one outlet nozzle, and
wherein an outflow direction (w) of the at least one second inlet nozzle and the outflow direction (v) of the at least one first inlet nozzle are directed in an angular relation to each other and/or in different planes.

* * * * *